US008083702B2

(12) United States Patent
Ashihara

(10) Patent No.: US 8,083,702 B2
(45) Date of Patent: Dec. 27, 2011

(54) WALKING ASSISTANCE DEVICE

(75) Inventor: Jun Ashihara, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 402 days.

(21) Appl. No.: 12/247,466

(22) Filed: Oct. 8, 2008

(65) Prior Publication Data

US 2009/0099494 A1 Apr. 16, 2009

(30) Foreign Application Priority Data

Oct. 12, 2007 (JP) ................................ 2007-266136

(51) Int. Cl.
*A61F 5/00* (2006.01)
*A61H 1/00* (2006.01)

(52) U.S. Cl. .................. 602/23; 602/18; 602/16; 601/5

(58) Field of Classification Search .................... 602/19, 602/16, 23, 26, 27, 18; 601/5, 33, 34; 607/48, 607/49; 482/66, 128
See application file for complete search history.

(56) References Cited

U.S. PATENT DOCUMENTS 5,020,790 A * 6/1991 Beard et al. ....................... 482/4

FOREIGN PATENT DOCUMENTS

JP 4-501227 3/1992
JP 2007-020909 2/2007

* cited by examiner

*Primary Examiner* — Patricia Bianco
*Assistant Examiner* — Ophelia Hawthorne
(74) *Attorney, Agent, or Firm* — Rankin, Hill & Clark LLP

(57) ABSTRACT

A walking assistance device has a leg link formed by connecting a first link member and a second link member through a third joint assembly. A force generated at the leg link by driving the third joint assembly is transmitted to the body of a user. The walking assistance device enables the user to deeply squat by making the third joint assembly highly bendable. The third joint assembly has with a joint link member, a first joint which connects the joint link member and a first link member, and a second joint which connects the joint link member and the second link member. The walking assistance device is further equipped with a drive source which imparts a torque in a stretching direction to the first joint, and an elastic member which elastically holds the second joint in a predetermined stretched state until a predetermined value or more acts thereon.

18 Claims, 6 Drawing Sheets

WALKING ASSISTANCE DEVICE

BACKGROUND OF THE INVENTION

1. Field of the Invention

The present invention relates to a walking assistance device which reduces a load acting on a leg or legs of a user thereby to assist walking of the user.

2. Description of the Related Art

Hitherto, as this type of walking assistance device, there has been known one equipped with a load transmitting assembly, foot-mounted assemblies to be attached to the feet of a user, and leg links between the load transmitting assembly and the foot-mounted assemblies. The walking assistance device is adapted to transmit forces from the leg links to the body trunk of the user through the intermediary of the load transmitting assembly, thereby permitting a reduction in load acting on the legs of the user (refer to, for example, Japanese Patent Application Laid-Open No. 2007-20909).

In this walking assistance device, each of the leg links includes an upper first link member connected to the load transmitting assembly through the intermediary of a first joint, a lower second link member connected to the foot-mounted assembly through the intermediary of a second joint, and an intermediate third joint assembly which bendably connects the first link member and the second link member. A torque in a stretching direction, i.e., in a direction for reducing the bending angle between the first and the second link members, is imparted to the third joint assembly by a drive source, to generate an assisting force in each of the leg links to support a part of the weight of the user.

Here, laterally offsetting the second link member with respect to the first link member leads to an increased breadth of the entire leg link, causing the leg link to easily come in contact with a leg of the user. For this reason, the first link member and the second link member are desirably connected without the lateral offsetting.

This, however, would inconveniently restrict the maximum bending angle at the third joint assembly to a relatively small angle due to the mutual interference between the first link member and the second link member in the vicinity of the third joint assembly, thus preventing the user from squatting deeply.

SUMMARY OF THE INVENTION

The present invention has been made with a view of the background described above, and it is an object of the invention to provide a user-friendly walking assistance device which permits a sufficiently large maximum bending angle at a third joint assembly thereby to allow a user to deeply squat.

To this end, in a walking assistance device equipped with a load transmitting assembly, a foot-mounted assembly to be attached to a foot of a user, and a leg link between the load transmitting assembly and the foot-mounted assembly, wherein the leg link includes an upper first link member connected to the load transmitting assembly through the intermediary of a first joint, a lower second link member connected to the foot-mounted assembly through the intermediary of a second joint, and an intermediate third joint assembly which bendably connects the first link member and the second link member, and the third joint assembly is driven to transmit a force generated in a leg link to the body trunk of the user through the intermediary of the load transmitting assembly, the present invention is characterized in that the third joint assembly is constructed as described below. In the present invention, the third joint assembly is characterized by having a joint link member provided between the first link member and the second link member, a first joint which bendably connects the joint link member and the first link member at an upper end portion of the joint link member, and a second joint which bendably connects the joint link member and the second link member at a lower end portion of the joint link member.

According to the present invention, the first link member and the second link member will be connected such that they are apart from each other by the length of the joint link member, i.e., by the axis-to-axis distance between the first joint and the second joint. Therefore, the chances of the mutual interference between the first link member and the second link member will be minimized without the need for the lateral offsetting of the first link member and the second link member. Thus, the bending angle at the third joint assembly, i.e., the bending angle between the first and the second link members, can be expanded to an angle in the vicinity of 180 degrees. This permits improved user-friendliness to be achieved, enabling the user to deeply squat with the walking assistance device attached to himself/herself.

Here, to generate an assisting force in each of the leg links for supporting a part of the weight of the user, it is necessary to impart a torque in the stretching direction, i.e., the direction for reducing the bending angle between the first and the second link members and the joint link member, to the first and the second joints. In this case, if the torque were imparted to each of the joints by an individual drive source, then two drive sources would be required, leading to an increased weight and higher cost. The present invention, therefore, is preferably equipped with a drive source for imparting a torque in the stretching direction to one of the first joint and the second joint and with an elastic member for elastically retaining the other joint in a predetermined stretched state. This arrangement allows an assisting force for supporting a part of the weight of a user to be generated in each of the leg links by a single drive source, making it possible to obviate an increase in weight and cost. Further, if a large moment acts on the third joint assembly when, for example, the user squats, then the other joint bends from the stretched state against an urging force of the elastic member, thus generating an assisting force equivalent to the urging force of the elastic member in the leg link. This allows load on the drive source to be reduced, achieving energy saving.

In this case, preferably, the walking assistance device is provided with a stopper for preventing one joint from moving in the direction in which the bending angle of one joint further increases after increasing to a predetermined angle, and the other joint is retained in a predetermined stretched state by the elastic member until the bending angle of one joint increases to the predetermined angle. This arrangement makes it possible to positively control the assisting force to be generated in the leg link by the drive source without being influenced by the elastic member until the bending angle of one joint increases to the predetermined angle. After the bending angle of one joint increases to the predetermined angle when, for example, the user squats, the other joint bends against the urging force of the elastic member, switching to a state wherein the assisting force is produced by the urging force of the elastic member.

Here, in the state wherein the bending angle of one joint is the predetermined angle, the assisting force is produced by the urging force of the elastic member, so that imparting a torque in the stretching direction by the drive source to one joint would be wasteful. Hence, in this state, imparting a torque to one joint by the drive source is preferably stopped to save energy.

DESCRIPTION OF THE PREFERRED EMBODIMENTS

Figure 1:
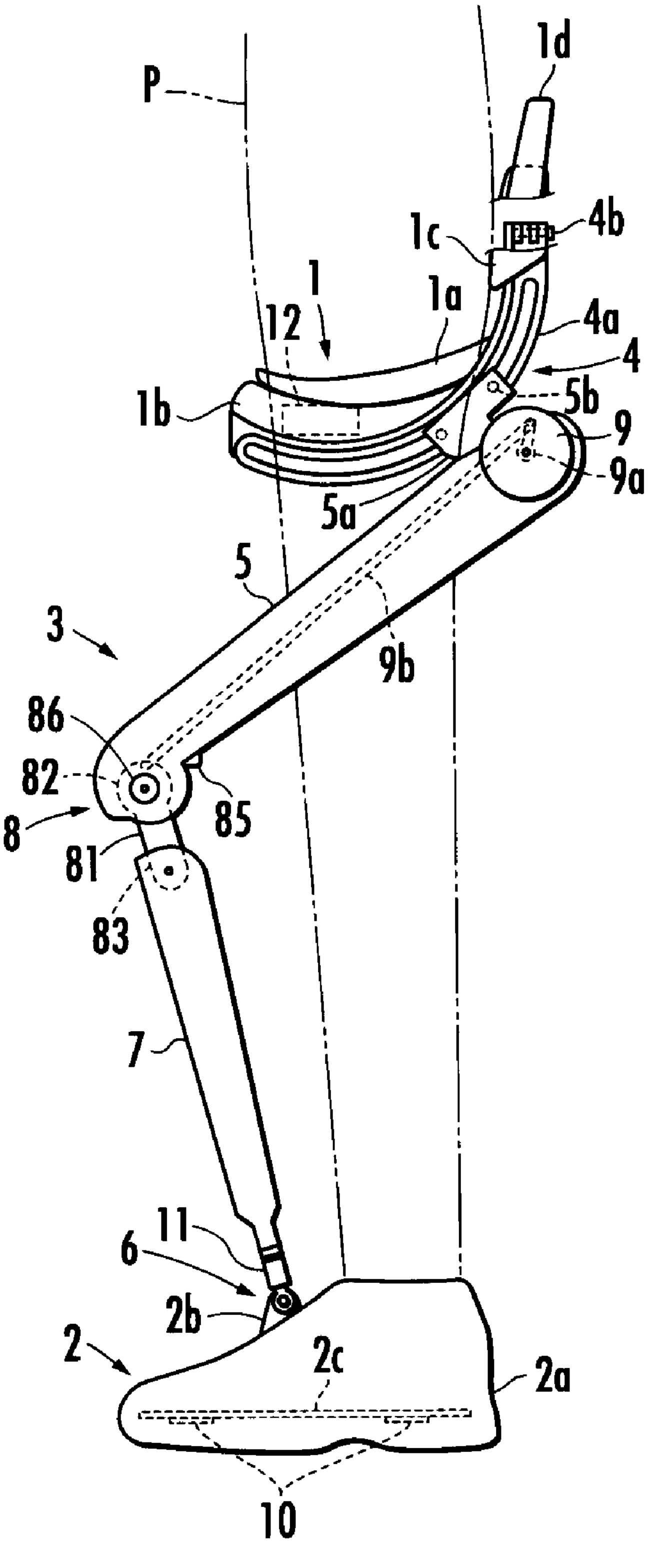
FIG. 1 is a side view of a walking assistance device of an embodiment in accordance with the present invention.
Figure 2:
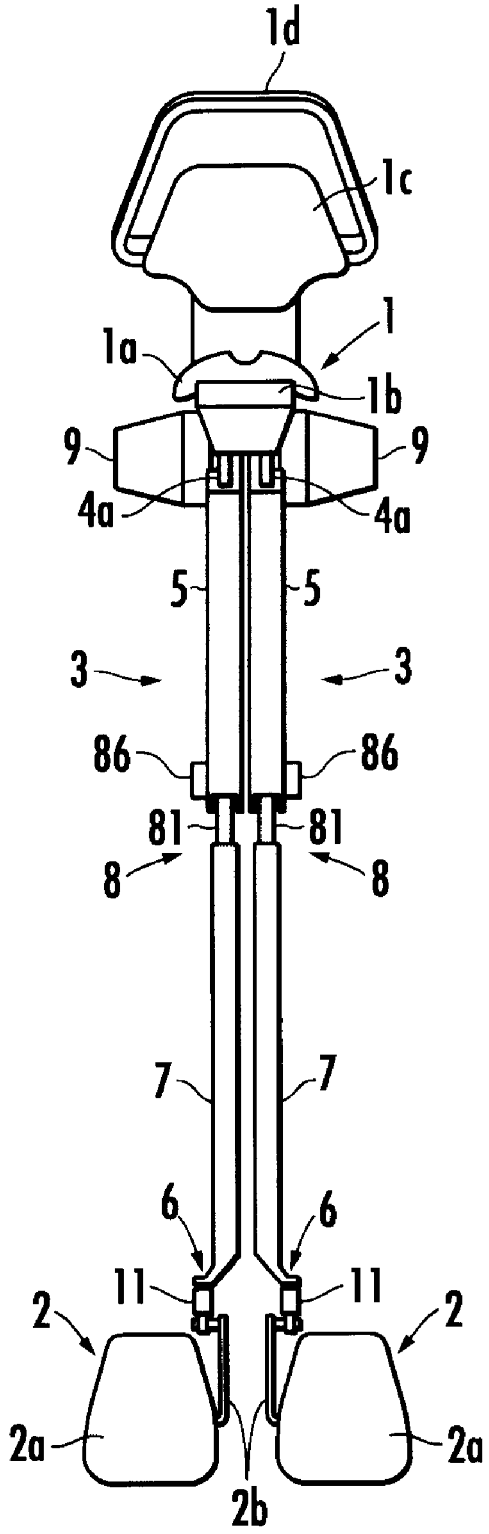
FIG. 2 is a front view of the walking assistance device of the embodiment.

The following will describe a walking assistance device according to an embodiment of the present invention. As illustrated in FIG. 1 and FIG. 2, the walking assistance device is equipped with a seating member 1 serving as a load transmitting assembly over which a user P strides to sit thereon, a pair of right and left foot-mounted assemblies 2 and 2 to be attached to the right and left feet of the user, and a pair of right and left leg links 3 and 3 provided between the seating member 1 and the right and left foot-mounted assemblies 2 and 2.

Each of the leg links 3 is constituted of an upper first link member 5 connected to the seating member 1 through the intermediary of a first joint assembly 4 such that each of the leg links 3 is free to longitudinally swing, a lower second link member 7 connected to the foot-mounted assembly 2 through the intermediary of a second joint 6, and an intermediate third joint assembly 8 (hereinafter also referenced as "third joint assembly 8") which bendably connects the first link member 5 and the second link member 7.

A drive source 9 for the third joint assembly 8, which is composed of an electric motor with a speed reducer, is mounted on the upper end portion of the first link member 5. A torque in a stretching direction, i.e., in the direction for reducing the bending angle between the first and the second link members 5 and 7, is imparted to the third joint assembly 8 by the drive source 9 so as to generate in the leg link 3 an assisting force for supporting a part of the weight of the user P. The assisting force generated in each of the leg links 3 is transmitted to the body trunk of the user P through the intermediary of the seating member 1, thus reducing the load acting on the legs of the user P.

The seating member 1 includes a saddle-like seat 1*a* on which the user P sits, a supporting frame 1*b* positioned under the seat 1*a* to support the seat 1*a*, and a hip pad 1*c* attached to the rising portion at the rear end of the supporting frame 1*b* which rises at the rear of the seat 1*a*. Further, the hip pad 1*c* is provided with an arched handle 1*d* which the user P can hold.

In a state wherein the user P is sitting on the seating member 1, the leg links 3 are positioned on the laterally inner side of the legs of the user P. Hence, when the walking assistance device is used, the seating member 1 and the leg links 3 are positioned under the crotch of the user, so that the user's hands will not come in contact with the seating member 1 or the leg links 3 when the user swings his/her arms in walking, thus permitting unimpeded arm swings. This results in improved user-friendliness.

Further, the first joint assembly 4 at the upper end of each of the leg links 3 has an arcuate guide rail 4*a* provided under the seating member 1. Each of the leg links 3 is movably engaged with the guide rail 4*a* through the intermediary of a plurality of rollers 5*b* rotatably attached to a slider 5*a* secured to the upper end portion of the first link member 5. Thus, each of the leg links 3 longitudinally swings about the center of the curvature of the guide rail 4*a*, and the longitudinal swing support point of each of the leg links 3 provides the center of the curvature of the guide rail 4*a*.

The guide rail 4*a* is rotatably supported by the rising portion at the rear end of the supporting frame 1*b* of the seating member 1 through the intermediary of a longitudinal spindle 4*b*. Thus, the guide rail 4*a* is connected to the seating member 1 such that it is laterally swingable, allowing each of the leg links 3 to laterally swing. This permits the abduction of each of the legs of the user P. The center of the curvature of the guide rail 4*a* and the axis line of the spindle 4*b* are positioned above the seat 1*a*. This arrangement makes it possible to prevent the seating member 1 from significantly inclining vertically or horizontally when the weight of the user P moves.

Each of the foot-mounted assemblies 2 is equipped with a shoe 2*a* and a connecting member 2*b* which is secured to the shoe 2*a* and which extends upward. Further, a second link member 7 of each of the leg links 3 is joined to the connecting member 2*b* through the intermediary of the second joint 6 having three axes. As illustrated in FIG. 1, a pair of front and rear pressure sensors 10 and 10 for detecting loads acting on a metatarsophalangeal joint (MP joint) portion and a heel portion of a foot of the user P is attached to the bottom surface of an insole 2*c* provided in the shoe 2*a*. Further, the second joint 6 incorporates a two-axis force sensor 11. The detection signals of the pressure sensors 10 and the force sensor 11 are input to a controller 12 accommodated in the supporting frame 1*b* of the seating member 1. The controller 12 controls the drive source 9 on the basis of the detection signals from the pressure sensor 10 and the force sensor 11 to drive the third joint assembly 8 of the leg link 3, thereby conducting walking assistance control for generating the aforesaid assisting force.

Here, an assisting force acts on a line which connects the longitudinal swing support point of the leg link 3 at the first joint assembly 4 and the longitudinal swing support point of the leg link 3 at the second joint 6, as observed from a lateral direction (hereinafter referred to as the reference line). Hence, in the walking assistance control, an actual assisting force (to be precise, the resultant force of an assisting force and a force attributable to the weights of the seating member 1 and each of the leg links 3) acting on the reference line is calculated on the basis of the detection values of the forces in the directions of two axes detected by the force sensor 11. Further, the ratio of operating load of each foot with respect to the total load acting on both feet of the user P is calculated on the basis of the detected pressure of the pressure sensor 10 of each of the foot-mounted assemblies 2. Subsequently, the value obtained by multiplying a set value of assisting force which is set in advance by the ratio of load of each foot is calculated as a control target value of the assisting force to be generated at each of the leg links 3. Then, the drive source 9 is controlled such that the actual assisting force calculated on the basis of the detection values of the force sensor 11 becomes the control target value.

Meanwhile, in order to prevent the leg links 3 from coming in contact with the legs of the user P, it is necessary to connect the first link member 5 and the second link member 7 without laterally offsetting them and to minimize the breadth of the leg link 3. In this case, directly connecting the first link member 5 and the second link member 7 at the third joint assembly 8 would cause the first link member 5 and the second link member 7 to interfere with each other in the vicinity of the third joint assembly 8, thus restricting the maximum bending angle at the third joint assembly 8 to a relatively small angle. This would prevent the user P from deeply squatting.

Figure 3:
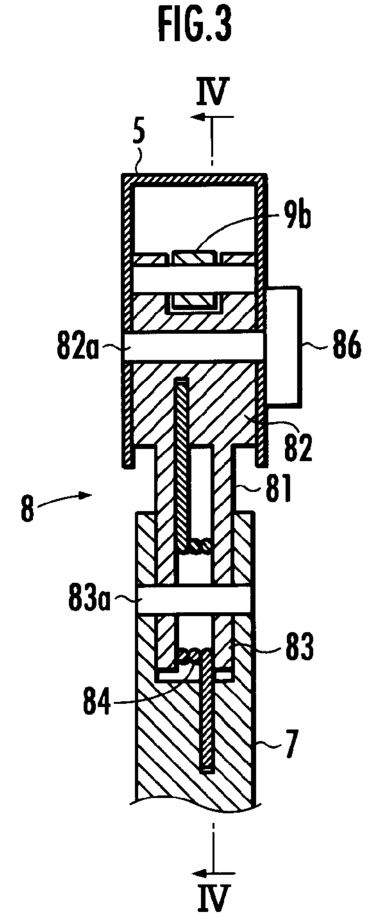
FIG. 3 is a longitudinal sectional view of a third joint assembly of the walking assistance device of the embodiment.
Figure 4:
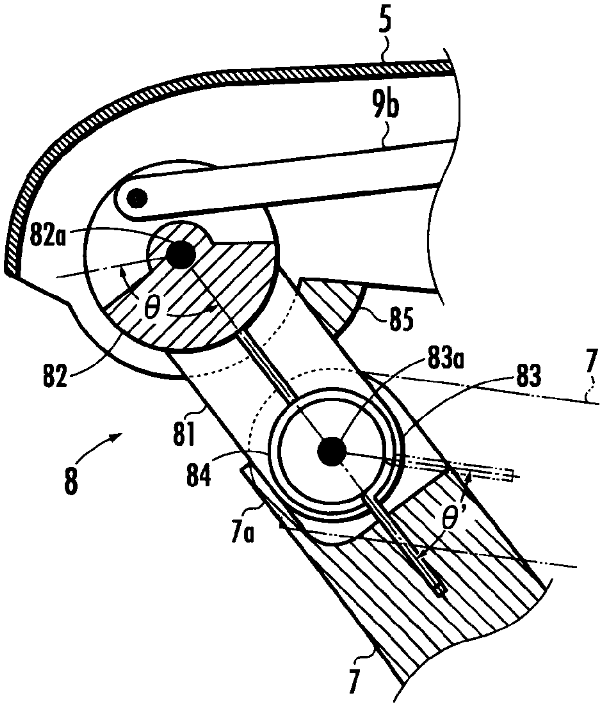
FIG. 4 is a side view cut at the line IV-IV of FIG. 3.

To avoid the aforesaid problem, as illustrated in FIG. 3 and FIG. 4, according to the present embodiment, the third joint assembly 8 is constituted of a joint link member 81 provided between the first link member 5 and the second link member 7, a first joint 82 which connects the joint link member 81 and the first link member 5 at the upper end portion of the joint link member 81 such that they may bend or stretch about a shaft 82*a*, and a second joint assembly 83 which connects the joint link member 81 and the second link member 7 at the lower end portion of the joint link member 81 such that they may bend or stretch about a shaft 83*a*.

Figure 5:
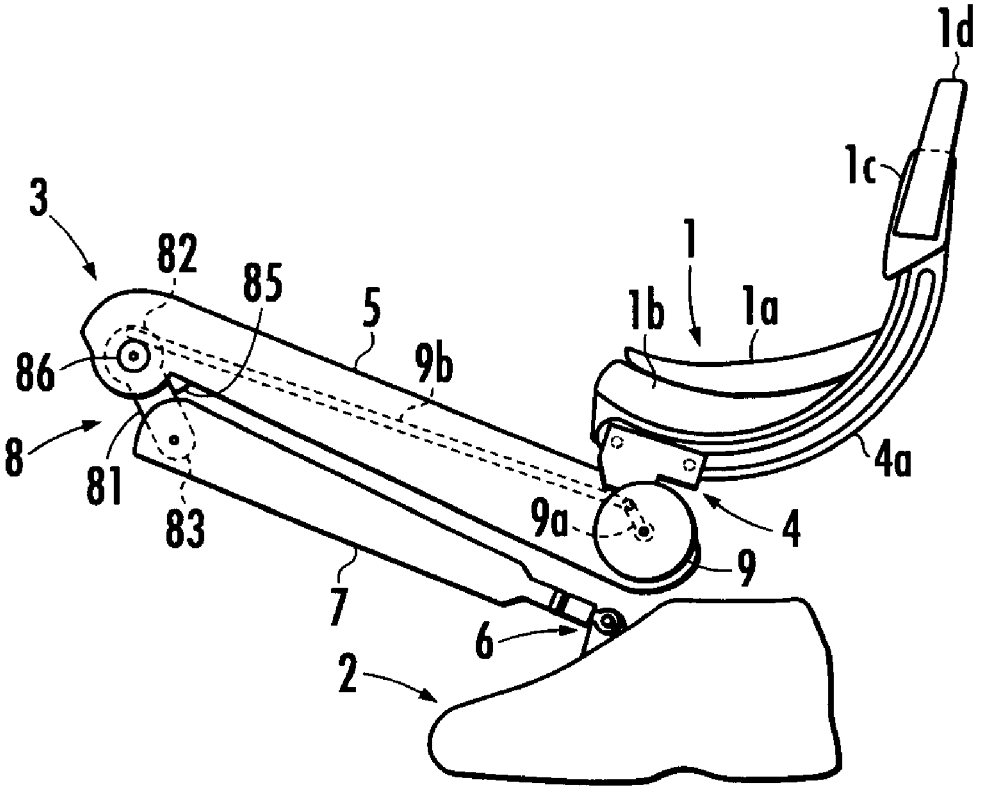
FIG. 5 is a side view illustrating a state wherein a user of the walking assistance device of the embodiment is squatting.

With this arrangement, the first link member 5 and the second link member 7 are connected while they are set apart by the length of the joint link member 81 (the axis-to-axis distance between the first joint 82 and the second joint assembly 83), thus minimizing the chances of the first link member 5 and the second link member 7 from interfering with each other. This makes it possible to increase the bending angle at the third joint assembly 8 (the bending angle between the first and the second link members 5 and 7) to an angle in the vicinity of 180 degrees, as illustrated in FIG. 5, allowing the user to deeply squat while wearing the walking assistance device.

The other end of a transmission link 9*b* having its one end connected to a crank arm 9*a* at the output end of the drive source 9 is connected to the first joint 82. Thus, a torque in the stretching direction, i.e., the direction for reducing the bending angle between the first link member 5 and the joint link member 81, is imparted to the first joint 82 by the drive source 9 through the intermediary of the transmission link 9*b*.

Further, the second joint assembly 83 is provided with an elastic member 84 which elastically retains the second joint assembly 83 in a predetermined stretched state (e.g., a state wherein the joint link member 81 and the second link member 7 are stretched straight), as illustrated in FIG. 3 and FIG. 4. This restrains the second joint assembly 83 from bending by itself, obviating the need for imparting a torque in the stretching direction to the second joint assembly 83 by a dedicated drive source. Therefore, it is possible to generate an assisting force in the leg link 3 by imparting the torque in the stretching direction to only the first joint 82 by the drive source 9.

Here, the elastic member 84 is composed of a torsion coil spring disposed to surround the shaft 83*a* of the second joint assembly 83 while one end and the other end of the shaft 83*a* are secured to the joint link member 81 and the second link member 7, respectively. The elastic member 84 applies, from the beginning, an urging torque for swinging the joint link member 81 counterclockwise in FIG. 4 with respect to the second link member 7 to the second joint assembly 83. Further, the second link member 7 is provided with a stopper 7*a* for preventing the joint link member 81 from swinging counterclockwise relative to the second link member 7 beyond the position at which the second link member 7 and the joint link member 81 are stretched straight, thereby elastically holding the second joint assembly 83 in the stretched state.

Figure 6:
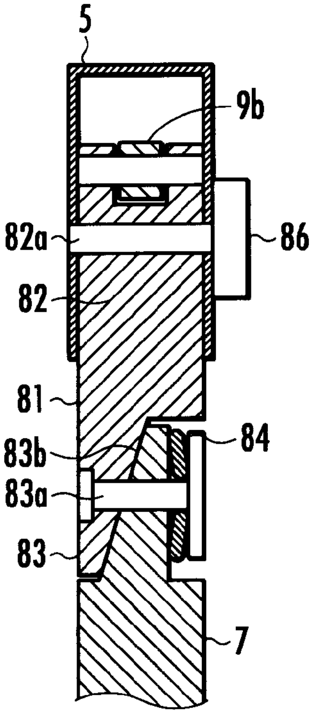
FIG. 6 is a longitudinal sectional view illustrating a modified example of the third joint assembly of the walking assistance device of the embodiment.

The elastic member 84 is not limited to the torsion coil spring. For example, as illustrated in FIG. 6, if a joining surface 83*b* between the joint link member 81 and the second link member 7 in the second joint assembly 83 is formed to be a spiral surface which causes the second link member 7 to displace laterally outward relative to the joint link member 81 as the bending angle at the second joint assembly 83 increases, then the elastic member 84 may be composed of a disc spring which presses the second link member 7 laterally inward.

Further, the present embodiment is provided with a stopper 85 which prevents the first joint 82 from further moving in the direction in which a bending angle θ at the first joint 82 (the bending angle of the joint link member 81 with respect to the extended line of a line connecting the shaft 82*a* of the first joint 82 and the axial center of the drive source 9) increases once the bending angle θ has increased to a predetermined angle. The stopper 85 is fixed to the first link member 5, and the joint link member 81 comes in contact with the stopper 85 when the bending angle θ at the first joint 82 reaches the predetermined angle. The stopper 85 may alternatively be secured to the joint link member 81.

Figure 7:
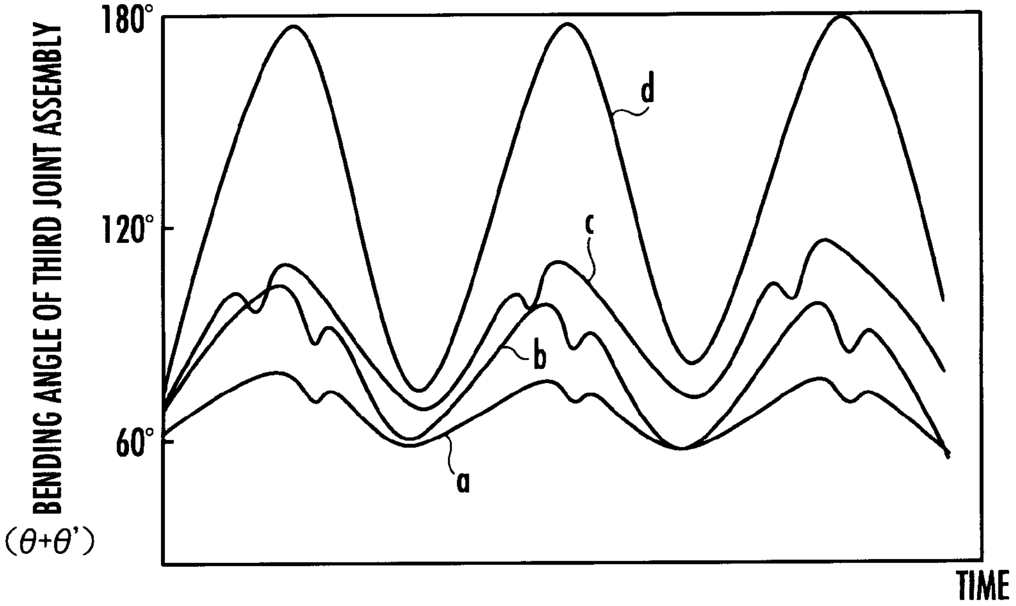
FIG. 7 is a graph illustrating changes in the bending angle of the third joint assembly which take place in response to various motions of the user.

FIG. 7 illustrates changes in the bending angle of the third joint assembly 8 (bending angle θ at the first joint 82+bending angle θ' at the second joint assembly 83) which take place in response to various motions of the user P. Line a in FIG. 7 indicates a change in the bending angle observed when the user P is walking on a flat ground, line b indicates a change when the user P is going up stairs, line c indicates a change when the user P is coming down the stairs, and line d indicates a change when the user P is repeating squatting and rising. As is obvious from FIG. 7, the bending angle of the third joint assembly 8 does not exceed 120 degrees in standard motions, such as walking on a flat ground or going up or down stairs. According to the present embodiment, therefore, the predetermined angle at which the stopper 85 is engaged is set to 120 degrees.

With this arrangement, for a standard motion of the user P, the torque to be imparted to the first joint 82 from the drive source 9 is variably set in the aforesaid walking assistance control, thus allowing the assisting force to be generated at the leg links 3 to be positively controlled. If the bending angle θ of the first joint 82 increases to 120 degrees when the user P squats, then the stopper 85 is engaged, so that a moment will be intensively applied to the second joint assembly 83 thereafter, causing the second joint assembly 83 to bend against an urging force of the elastic member 84. In this state, an assisting force equivalent to an urging torque attributable to a reaction force of the elastic member 84 is generated in the leg link 3.

Figure 8:
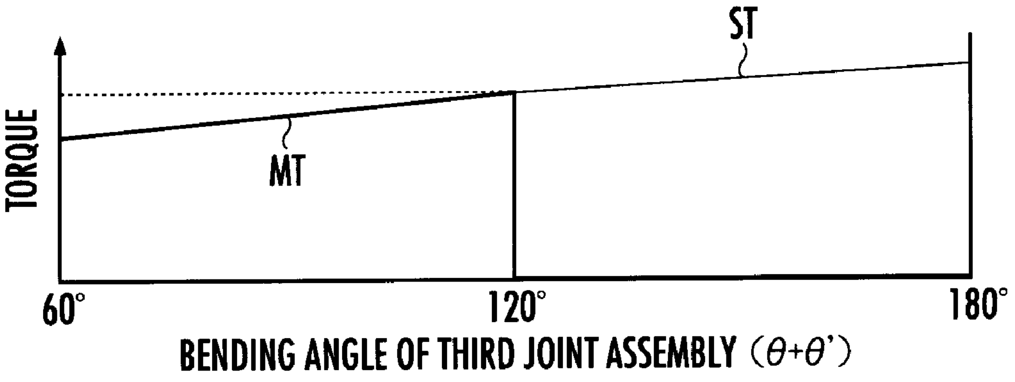
FIG. 8 is a graph illustrating a change characteristic of the torque imparted to each of a first and a second joints of the third joint assembly based on bending angles.

Here, even if the assisting force generated at the leg link 3 remains the same, the torque to be imparted to the third joint assembly 8 increases as the bending angle of the third joint assembly 8 increases. The torque imparted to the first joint 82 from the drive source 9 by the walking assistance control described above increases as the bending angle θ at the first joint 82 increases, as indicated by line MT in FIG. 8, and reaches a maximum when the bending angle θ reaches 120 degrees at which the bending angle θ is restricted by the stopper 85.

The initial urging torque to be imparted by the elastic member 84 to the second joint assembly 83, i.e., the torque for holding the second joint assembly 83 in a stretched state, is set to a value not less than a maximum value of the torque (the torque when θ is 120 degrees) to be imparted to the first joint

82 by the drive source 9 in the walking assistance control. Hence, the second joint assembly 83 is retained in the stretched state until the bending angle θ at the first joint 82 reaches 120 degrees. When the bending angle θ reaches 120 degrees, the second joint assembly 83 bends thereafter. Further, the urging torque imparted to the second joint assembly 83 from the elastic member 84 increases as the bending angle θ' at the second joint assembly 83 increases, as indicated by line ST in FIG. 8.

Thus, in an area wherein the bending angle of the third joint assembly 8 is 120 degree or more, a large torque to be imparted to the third joint assembly 8 will be supplied from the elastic member 84, making it possible to reduce the load on the drive source 9 with resultant energy saving. Further, in the present embodiment, an initial urging torque imparted to the second joint assembly 83 by the elastic member 84 is set to be equivalent to the maximum value of the torque to be imparted to the first joint 82 by the drive source 9 in the walking assistance control. With this arrangement, it is possible to restrain an assisting force generated in the leg link 3 from considerably changing beyond the bending angle of 120 degrees.

Even if the initial urging torque to be imparted to the second joint assembly 83 by the elastic member 84 has been set at a value that is larger than the maximum value of the torque imparted to the first joint 82 by the drive source 9 in the walking assistance control, significant changes in the assisting force beyond the 120-degree bending angle can be restrained by correcting the torque to be imparted to the first joint 82 by increasing the torque when the bending angle θ at the first joint 82 reaches a predetermined transient angle, which is smaller than 120 degrees, or more. For instance, if it is assumed that the transient angle is 100 degrees, and the difference between the initial urging torque imparted to the second joint assembly 83 by the elastic member 84 and the maximum value of the torque to be imparted to the first joint 82 by the drive source 9 in the walking assistance control is denoted by ΔT, then in the area defined by θ>100 degrees, a torque obtained by adding a correction torque of ΔT×(θ−100 degrees)/20 degrees to a torque required to generate an assisting force of a set value is imparted to the first joint 82. With this arrangement, the torque imparted to the first joint 82 when the bending angle θ reaches 120 degrees will be equal to the initial urging torque imparted to the second joint assembly 83 by the elastic member 84.

Incidentally, in the area wherein the bending angle at the third joint assembly 8 is 120 degrees or more, imparting a torque to the first joint 82 from the drive source 9 would be wasteful. According to the present embodiment, therefore, the third joint assembly 8 is provided with an angle sensor 86 for detecting the bending angle θ at the first joint 82, as illustrated in FIG. 3, and a detection signal of the angle sensor 86 is input to the controller 12 to switch the control of the drive source 9 on the basis of the bending angle θ at the first joint 82.

Figure 9:
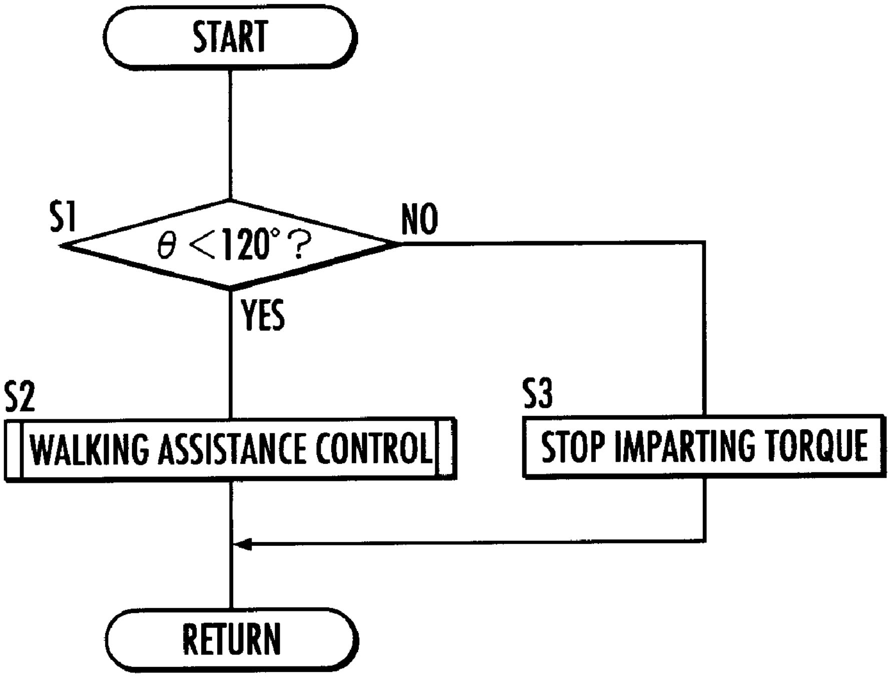
FIG. 9 is a flowchart illustrating the switching of control of a drive source in the walking assistance device of the embodiment.

The details are as illustrated in FIG. 9. First, in step S1, it is determined whether the bending angle θ at the first joint 82 detected by the angle sensor 86 is in a movable range, i.e., if θ<120 degrees. If θ<120 degrees, then the procedure proceeds to step S2 to carry out the walking assistance control described above. On the other hand, if θ=120 degrees, then the procedure proceeds to step S3 to interrupt energizing the drive source 9 so as to stop imparting a torque to the first joint 82 by the drive source 9. This prevents the drive source 9 from being wastefully driven in the area wherein the bending angle at the third joint assembly 8 is 120 degrees or more, permitting further improved energy saving.

Alternatively, instead of the angle sensor 86, a detection switch, such as a limit switch, for detecting contact of the joint link member 81 with the stopper 85 may be provided, and imparting a torque to the first joint 82 may be interrupted when the detection switch turns on.

The above has described the embodiment of the present invention with reference to the accompanying drawings; the present invention, however, is not limited thereto. For instance, the second joint assembly 83 may be provided with a drive source for imparting torques and an elastic member for elastically holding the first joint 82 in a predetermined stretched state. Further, in the aforesaid embodiment, the joint link member 81 has been constituted of a single rod material; alternatively, however, the joint link member 81 may be composed by bendably connecting two or more rods. In this case, a joint for connecting together the rods constituting the joint link member 81 will be provided between the first joint 82 and the second joint assembly 83. The joint will be elastically held at a predetermined stretched state by an elastic member similar to the aforesaid elastic member.

In the aforesaid embodiment, the first joint assembly 4 has been constructed to have the arcuate guide rail 4*a*, so that the longitudinal swing support point of each of the leg links 3 at the first joint assembly 4 is positioned above the seat la of the seating member 1; however, the structure of the first joint assembly 4 is not limited thereto. For example, the first joint assembly 4 may be constructed of a simply structured joint assembly having a shaft which rotatably supports the upper end portion of each of the leg links 3 such that the upper end portion is free to swing in the longitudinal direction.

In the aforesaid embodiment, the seating member 1 constitutes the load transmitting assembly; alternatively, however, the load transmitting assembly may be constituted of a harness to be worn around the waist of a user. Furthermore, to assist walking of a user with one leg crippled due to bone fracture or the like, the leg link mechanism of only one of the right and left leg links 3 and 3 in the aforesaid embodiment, whichever is to support the crippled leg of the user, may be left and the leg link mechanism of the other leg link may be omitted.

What is claimed is:

1. A walking assistance device comprising:

a load transmitting assembly;

a foot-mounted assembly to be attached to a foot of a user; and a leg link between the load transmitting assembly and the foot-mounted assembly, wherein the leg link comprises an upper first link member connected to the load transmitting assembly through an intermediary of a first joint assembly, a lower second link member connected to the foot-mounted assembly through an intermediary of a second joint assembly, and an intermediate third joint assembly which bendably connects the upper first link member and the lower second link member, a force generated in the leg link by driving the intermediate third joint assembly is transmitted to a body trunk of the user through an intermediary of the load transmitting assembly, and the intermediate third joint assembly comprises a joint link member provided between the upper first link member and the lower second link member, a first link member joint which bendably connects the joint link member and the upper first link member at an upper end portion of the joint link member, and a second link member joint which bendably connects the joint link member and the lower second link member at a lower end portion of the joint link member, the upper first link member and the lower second link member being set apart from one another by the length of the joint link member.

2. The walking assistance device according to claim 1, wherein the joint link member, the first link member joint, and the second link member joint are integrally formed as a unitary piece with the first link member joint disposed at the upper end portion of the joint link member and the second link member joint disposed at the lower end portion of the joint link member.

3. The walking assistance device according to claim 2, wherein the first link member joint bendably connects the joint link member to a lower end portion of the upper first link member and the second link member joint bendably connects the joint link member to an upper end portion of the lower second link member.

4. The walking assistance device according to claim 3, wherein the first link member joint is rotatably connected to the lower end portion of the upper first link member via a first shaft which passes through and engages the first link member joint and the lower end portion of the upper first link member, and the second link member joint is rotatably connected to the upper end portion of the lower second link member via a second shaft which passes through and engages the second link member joint and the upper end portion of the lower second link member.

5. The walking assistance device according to claim 1, wherein the upper first link member is only connected to the lower second link member through the respective bendable connections to the joint link member.

6. The walking assistance device according to claim 1, wherein the bendable connection of the upper first link member to the lower second link member through the intermediate third joint assembly is configured to allow a bending angle between the upper first link member and the lower second link member to exceed 120 degrees.

7. A walking assistance device comprising:

a load transmitting assembly;

a foot-mounted assembly to be attached to a foot of a user;

a leg link between the load transmitting assembly and the foot-mounted assembly;

a drive source; and an elastic member, wherein the leg link comprises an upper first link member connected to the load transmitting assembly through an intermediary of a first joint assembly, a lower second link member connected to the foot-mounted assembly through an intermediary of a second joint assembly, and an intermediate third joint assembly which bendably connects the upper first link member and the lower second link member, a force generated in the leg link by driving the intermediate third joint assembly is transmitted to a body trunk of the user through an intermediary of the load transmitting assembly, the intermediate third joint assembly comprises a joint link member provided between the upper first link member and the lower second link member, a first link member joint which bendably connects the joint link member and the upper first link member at an upper end portion of the joint link member, and a second link member joint which bendably connects the joint link member and the lower second link member at a lower end portion of the joint link member, the drive source is configured to impart a torque in a stretching direction to one of the first link member joint and the second link member joint, the elastic member is configured to elastically hold one of the first link member joint and the second link member joint in a predetermined stretched state, and the torque imparted link member joint is different from the elastically held link member joint.

8. The walking assistance device according to claim 7, further comprising:

a stopper configured to prevent the torque imparted link member joint from moving in a direction in which a bending angle at the torque imparted link member joint further increases after the bending angle increases to a predetermined angle, wherein the elastically held link member joint is retained in the predetermined stretched state by the elastic member until the bending angle of the torque imparted link member joint increases to the predetermined angle.

9. The walking assistance device according to claim 8, wherein the drive source is configured to stop imparting a torque to the torque imparted link member joint when the bending angle of the torque imparted link member joint is greater than or equal to the predetermined angle.

10. The walking assistance device according to claim 8, wherein the predetermined angle is 120 degrees.

11. The walking assistance device according to claim 8, wherein the stopper is fixed to the upper first link member.

12. The walking assistance device according to claim 7, further comprising an angle sensor configured to sense a bending angle at the torque imparted link member, and wherein the drive source is configured to stop imparting a torque to the torque imparted link member joint when the bending angle of the torque imparted link member joint is greater than or equal to a predetermined angle.

13. The walking assistance device according to claim 12, wherein the predetermined angle is 120 degrees.

14. The walking assistance device according to claim 7, wherein the elastic member is a torsion spring connected to the second link member joint and the lower second link member.

15. The walking assistance device according to claim 7, wherein the elastic member is a disc spring connected to the second link member joint and the lower second link member.

16. A walking assistance device comprising:

a load transmitting assembly;

a foot-mounted assembly to be attached to a foot of a user; and a leg link between the load transmitting assembly and the foot-mounted assembly, wherein the leg link comprises an upper first link member connected to the load transmitting assembly through an intermediary of a first joint assembly, a lower second link member connected to the foot-mounted assembly through an intermediary of a second joint assembly, and a single intermediate joint link member bendably connected to the first upper link member at an upper end portion of the single intermediate joint link member through a first joint, and bendably connected to the lower second link member at a lower end portion of the single intermediate joint link member through a second joint, and a force generated in the leg link by driving the single intermediate joint link member is transmitted to a body trunk of the user through an intermediary of the load transmitting assembly.

17. The walking assistance device according to claim 16, wherein the single intermediate joint link member is connected to the first upper link member and the second lower link member such that an intermediate transverse range of the single intermediate joint link member and a lower transverse range of the lower second link member are substantially equal to an upper transverse range of the upper first link member.

18. A walking assistance device comprising:

a first leg link member connected to a load transmitting assembly;

a second leg link connected to a foot-mounted assembly; and a joint link member having a body defining a length between a first link member joint disposed at an upper end portion of the joint link member body and a second link member joint disposed at a lower end portion of the joint link member body, the first leg link member bendably connecting to the first link member joint and the second leg link member bendably connecting to the second link member joint such that a lower end of the first leg link member is spaced from an upper end of the second leg link member by the length defined between the first link member joint and the second link member joint, wherein the first leg link member is only connected to the second leg link member via the joint link member.

* * * * *